United States Patent [19]

Friedman et al.

[11] 4,156,423
[45] May 29, 1979

[54] CORONARY ATHEROSCLEROSIS DIAGNOSTIC METHOD

[75] Inventors: Ernest H. Friedman, 1831 Forest Hills Blvd., East Cleveland, Ohio 44112; Charles M. Flammer, Brighton, Mass.; Daniel A. Baker, St. Joseph, Mich.

[73] Assignee: Ernest H. Friedman, East Cleveland, Ohio

[21] Appl. No.: 851,285

[22] Filed: Nov. 14, 1977

[51] Int. Cl.² ............................................... A61B 5/02
[52] U.S. Cl. ................................................. 128/695
[58] Field of Search ...................... 128/2.05 R, 2.05 S, 128/2 R

[56] References Cited
PUBLICATIONS

Friedman et al., "American Journal of the Medical Sciences" vol. 255, No. 4, Apr., 1960, pp. 237-244.
Szabadi, et al. "British Journal of Psychiatry" vol. 129, 1976, pp. 592-597.
Jaffe et al., "Rhythms of Dialogue" 1970, Academic Press, New York & London, Appendix A, pp. 123-142.

Primary Examiner—William E. Kamm
Attorney, Agent, or Firm—Pearne, Gordon, Sessions, McCoy & Granger

[57] ABSTRACT

Electronic apparatus is disclosed which is usable to determine the fluency of a person's speech. This apparatus may monitor a dialogue directly, may be connected to a telephone to monitor a dialogue, or may be connected to be responsive to a recording of the dialogue. The apparatus determines the number of hesitation pauses of joint silence of both persons bounded by speech uttered by the subject which pauses are in excess of a time interval in the order of one second of time. The apparatus gives an indication, either visible or audible, when the number of such pauses exceeds a presettable limit per unit of time. The apparatus may be used by the medical profession to determine a subject's proneness to clinical coronary atherosclerosis where the rate of such hesitation pauses is in excess of a presettable value. It may also be used by disc jockeys, sales personnel or the like.

8 Claims, 12 Drawing Figures

CORONARY ATHEROSCLEROSIS DIAGNOSTIC METHOD

BACKGROUND OF THE INVENTION

The determination of the likelihood of heart attacks or more technically, coronary atherosclerosis, has been of vital concern not only to the medical profession but to the population in general. The news media abound with accounts of a person dying from a "heart attack," yet it was reported that person had just had a complete physical check up and pronounced fit.

Diastolic and systolic blood pressure had been the typical indicator used to diagnose a person's proneness to clinical coronary atherosclerosis for many years, yet this indicator is far from being infallible and a better indicator is desired.

The prior art has attempted to determine the incidence and prevalence of coronary heart disease by many different methods and analyses. These include trying to determine the relationship of coronary risk to: occupational stress, education, sexual activity, annual income, behavior patterns, socioeconomic background and status.

Motor retardation, that is, slowness of movement and speech, has been studied as an indicator of depressive illness. The hesitation pause times in the subject's speech has been observed to be significantly elongated while the patients were mentally depressed.

The voice fluency monitor is a new method of electronic monitoring of non-lexical conversational style, i.e., hesitation pauses. A hesitation pause is defined in an interview dialogue as joint silence bounded by the speech of the subject. The working hypotheses in the present invention are that hesitation pauses reflect behavioral maladaptation and are related predictively to the development of coronary atherosclerosis. The relevance of this synthesis of psycholinguistics and cardiovascular research is portrayed by recent evidence supporting psychologic and social risk factors for coronary disease. Standard risk factors such as blood pressure, overweight, serum cholesterol taken together provide an incomplete estimate of the coronary disease burden of the population and an insensitive prediction of the risks of individuals. The need for simultaneous study of psychosocial and standard risk factors has been emphasized in order to shed light on pathophysiological mechanisms, and possibly provide insight for more effective disease programs. It is noted that several studies have already adhered to this design and in all of them it was found that the behavioral risk factor made an independent contribution to coronary risk after the influences of the standard biologic risk factors available for study were accounted for statistically.

Four separate studies have demonstrated a correlation of position in the socioeconomic hierarchy to coronary risk factors, morbidity and mortality. In Cleveland, Ohio attorneys, coronary morbidity and mortality correlated to socioeconomic background and status. The coronary prevalence rate of the top socioeconomic group was significantly less than that of the middle group but no significantly less than that of the lowest group. These attorneys exhibited a similar profile in terms of family history of diabetes mellitus in one or both parents and in the three year followup of coronary mortality.

The same pattern prevailed in a broader sample of an employed population in the Bell system ranging from executives to workmen. The greatest difference was between executives and foremen, the workmen being intermediate. Similar data were found in the Dupont Company hierarchy stratified into five economic groups, with Group I being the highest income group, and Group V the lowest income group. Groups I and II exhibited the lowest rates of myocardial infarction, diabetes mellitus and hypertension, Group III the highest, and Groups IV and V were intermediate.

Cleveland businessmen were stratified into three groups according to annual income. The top income group I was significantly different from the middle income group II but not significantly different from the bottom income group III in exhibiting lower resting diastolic blood pressure, greater self esteem as measured on The Minnesota Multiphasic Personality Inventory, more well-controlled aggression on an Inkblot Test and more vigor (Type A style) in response to the R. Rosenman-M. Friedman Structured Tape Recorded Interview designed to elicit Type A.

Compatible findings were obtained in a study of sexual activity and coronary risk. Long-standing maladaptation was hypothesized in recently coronary stricken subjects compared with normal coronary prone subjects. Coronary risk correlated with less outwardly directed activity as a defense against underlying passive dependency, more influence of the latter on a decline of sexual activity over 25 years of marriage, less annual income and fewer children. Greater unresolved dependency needs also were described in patients with arteriosclerotic heart disease compared with valvular rheumatic heart disease patents.

Accordingly, an object of the invention is to provide a solution to the problem of better diagnosis of proneness to clinical coronary atherosclerosis in human subjects.

SUMMARY OF THE INVENTION

The solution to the problem lies in utilizing the method of diagnosis of proneness to clinical coronary atherosclerosis in a human subject, comprising the steps of; having the subject utter oral speech, obtaining from either the speech directly or a recording of the speech a determination of the hesitation pauses of absence of vocal sounds within the speech uttered by the subject which pauses are in excess of a given time interval in the order of one second of time, determining the number of such pauses in a period of time of speech of the subject, and indicating the subject's greater proneness to the development of clinical coronary atherosclerosis where the rate of such pauses is in excess of a value in the order of two pauses per minute.

An object of the invention is to provide apparatus to provide an indication of the fluency of human speech.

Another object of the invention is to provide both a method and electronic apparatus to diagnose the proneness to clinical coronary atherosclerosis by determining the rate of hesitation pauses in the speech of a subject.

Another object of the invention is to provide a medical diagnosis tool for quick and ready determination of possible coronary heart disease.

Another object of the invention is to provide apparatus usable by either medical personnel or the subject himself for evaluation of voice fluency, especially in diagnosis of proneness to coronary heart disease.

DESCRIPTION OF THE PREFERRED EMBODIMENTS

Figure 1:
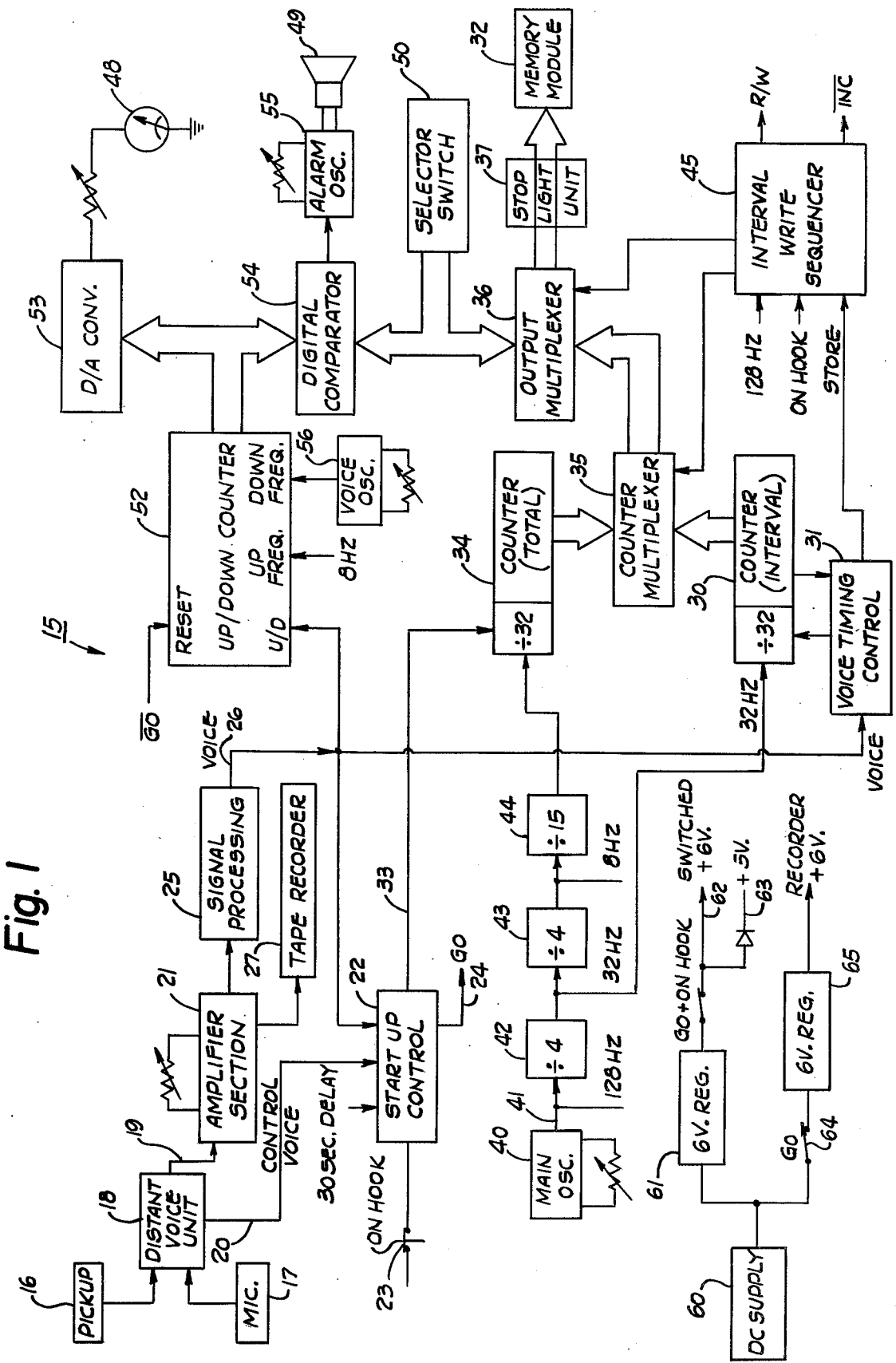
FIG. 1 is a block diagram of the entire voice fluency apparatus.

FIG. 1 is a general block diagram of the entire electronic apparatus. This apparatus may be used in a variety of ways and for a variety of purposes. The apparatus may be used with a person delivering a monologue or may be used with two persons having a dialogue. In the monologue application, the apparatus may be used by persons such as disc jockeys, news announcers, sales persons, etc., to determine the fluency of their speech pattern and more specifically to determine the number and duration of the hesitation pauses in their speech delivery. When the apparatus is used to monitor a dialogue, then it may be used by radio and television personalities, businessmen, executives, etc., again to determine the fluency of their speech patterns.

A more important aspect is the use of the apparatus and the method of using the apparatus in the medical field as a diagnostic tool. It may be used in the diagnosis of proneness to clinical coronary atherosclerosis in a human subject. It has been determined that a person has greater proneness to the development of clinical coronary atherosclerosis where the rate of his speech hesitation pauses is in excess of a value in the order of two pauses per minute. In this sense, a hesitation pause is defined as joint silence of both persons bounded by speech uttered by the subject which pauses are in excess of a time interval in the order of one second of time.

Accordingly, the apparatus as broadly defined is capable of determining the hesitation pauses of a subject, counting the number of such pauses, counting the total length of time of the speech and determining the rate of such pauses per unit of time. The apparatus also ignores those pauses which are within the speech of the doctor or interviewer, and ignores those pauses which are between the speech of the doctor and the subject or between the speech of the subject and the doctor. The apparatus may be used to provide an indication of the rate of such hesitation pauses in the subject's speech and this indication may be visible or audible. Also the data of the number of pauses and the length thereof may be committed to memory so that it may be printed on a record at a later time.

The apparatus is designed to be connected to a telephone as a convenient way of obtaining data from the speech of the subject. The voice fluency monitor may be connected to the telephone of the interviewer, such as a doctor, and then any ordinary telephone used by the subject under evaluation will provide the subject's speech data to the unit at the doctor's telephone. Accordingly, it will be seen that the equipment is quite versatile and has several uses and modes of operation.

FIG. 1 shows generally the block diagram of the voice fluency apparatus 15 which includes a pick-up 16 and a microphone 17. These are connected to a distant voice unit 18. Where the apparatus is used in a doctor's office, for example, the microphone 17 would be mounted adjacent the microphone of the telephone and the pick-up such as an electromagnetic pick-up mounted adjacent the earpiece of that same telephone. In such case the microphone would be responsive almost entirely to the voice of the doctor or interviewer whereas the pick-up 16 would be responsive to both the distant voice; namely, the voice of the subject, as well as the voice of the doctor. The distant voice unit 18 thus distinguishes between the times when the subject is speaking and the times when the doctor is speaking so that a true hesitation pause may be obtained; namely, joint silence of both parties bounded by speech of the subject; i.e., the distant voice.

The distant voice unit has an output on line 19 to an amplifier 21 and on line 20 the control voice, or doctor's voice signal is supplied to a start-up control 22. The start-up control 22 has an input from an ON HOOK switch 23 which is closed when the telephone instrument is on the hook and is opened when the telephone instrument is taken off the hook. This may be a switch separate from the regular telephone equipment, for example, a switch connected to the telephone instrument and a magnet to actuate the switch clipped onto the telephone hand set. The start-up control 22 provides a delay in completing actuation of the entire apparatus 15. This delay may be anything suitable, for example, 30 seconds and prevents the apparatus from becoming prematurely active when initiating a phone call. This delay allows time for dialing as well as delays that may occur when going through a switchboard or receptionist, thus insuring a conversation is well under way before the apparatus is activated. An additional delay is also provided, for example, eight seconds of talking is required before the apparatus becomes active. At the end of these two delay periods a signal appears on the GO output line 24 to activate the equipment.

Assuming that the apparatus 15 is used with two persons having a dialogue, then the pick-up 16 is used to obtain the distant voice of the subject, and his telephone equipment may be any ordinary telephone equipment with this apparatus 15 at the doctor's office, for example. The apparatus 15 obtains data from the speech of the subject and specifically this data is the number and duration of hesitation pauses within the speech of the subject. The amplifier section 21 amplifies the voice of the subject as an analog signal and passes to the signal processing section 25 where it is processed into a digital signal labeled VOICE in FIG. 1 on line 26 with this digital signal VOICE 26 being high if the subject is speaking and being low if the subject is silent. An optional tape recorder 27 may be supplied to record the subject's voice and optionally the doctor's voice.

When the subject is speaking, the apparatus 15 records no digital data. When the subject stops talking, i.e., when the pick-up 16 receives no sound input, an interval counter 30 starts counting. This interval counter is controlled by a voice timing control 31 by the VOICE signal 26. If the subject again commences to talk before a presettable time, for example, one-half second, the counter 30 is reset. If the subject talks after this preset time, the counter reading in seconds is recorded in a memory module 32 and then the interval counter 30 is reset. The start-up control 22 has an output on a line 33 to a total counter 34 which counts the length of total time of the telephone conversation. The outputs of the interval counter 30 and total counter 34 are multiplexed in a counter multiplexer 35 and passed to an output multiplexer 36, from that multiplexer through a stop light unit 37 to the memory module 32. The stop light unit 37 may be used to provide a visible indication such as red, yellow and green lights. This indicates to the person using the telephone whereat the apparatus 15 is located that the subject has too many hesitation pauses if the red light flashes, has a satisfactorily low number of hesitation pauses if the green light is illuminated, and indicates a borderline condition if the yellow light is illuminated.

A main oscillator 40 is provided for a clock frequency on a line 41, for example, of 128 hertz. This is divided by dividers 42, 43 and 44 to obtain lower frequency signals to be applied to the interval counter 30 and total counter 34. The voice timing control 31 controls an interval write sequencer 45 which has read and write outputs and increment outputs as well as outputs to the multiplexers 35 and 36.

A meter 48 is provided to give feedback to the subject, if he is using the apparatus 15 at his telephone. When the subject is not talking; namely, a hesitation pause, the meter needle rises at a constant rate reaching full scale in a certain time, e.g., ten seconds. An audible alarm 49 sounds when the meter needle goes past the time selected by a delay selector switch 50. This might be some period of time between one and twenty-four seconds, for example, it might be set at a ten second delay period. The meter needle drops at a different constant rate when the subject is speaking. The alarm will always be off while speech is occurring and will always be on if the needle is above the selected delay time while the subject's speech is absent. This meter and alarm are controlled by an up/down counter 52. This counter counts up while the subject is silent and counts down when the subject is talking. This counter is controlled by the VOICE line 26 and has an output to a digital to analog converter 53. The counter 52 also has an output to a digital comparator 54 which compares the count from the counter with a digital binary code from the counter 52 with the digital binary code from the delay selector switch 50, and enables the alarm 49 through an alarm oscillator 55 when the counter output is larger. When the subject is talking the counter 52 counts down using a frequency of a voice oscillator 56.

A DC supply source 60 supplies operating voltage for the apparatus 15 including supplying a six volt regulator 61 which supplies a SWITCHED +6V on conductor 62 to be used in the memory module 32 +5V on line 63 used generally in the apparatus 15, and through a GO switch 64 and a six volt regulated supply 65 to supply power to the optional recorder.

DETAILED DESCRIPTION

The voice fluency apparatus 15 may be used in several different ways and in general the equipment is designed to be used in connection with a telephone. The equipment may be used in connection with direct face to face dialogue between two persons but in order to save time for both the interviewer, for example, a doctor, and the subject or patient, the equipment may be used in conjunction with a telephone. The doctor may have the apparatus 15 in association with his telephone and then the subject may use any ordinary telephone instrument without the necessity for any equipment connected thereto.

Use of the distant voice unit 18 in connection with the apparatus 15 permits this mode of operation. Transducers 16 and 17 receive acoustic signals and transform them into electrical signals. The pick-up 16 near the earpiece of the doctor's receiver picks up both conversations and the microphone 17 near the mouthpiece of the doctor's telephone picks up primarily only the doctor's voice. If the subject is in the doctor's office and using the telephone with the apparatus 15 associated therewith, then the subject's voice may go into a microphone which is plugged into a jack 70 and nothing would be plugged into a jack 71, FIG. 2. Normally, however, with the equipment at the doctor's office and no equipment at the patient or subject's telephone, the earpiece pick-up 16 is plugged into the jack 70 and the doctor's microphone pick-up 17 is plugged into the jack 71.

Figure 2:
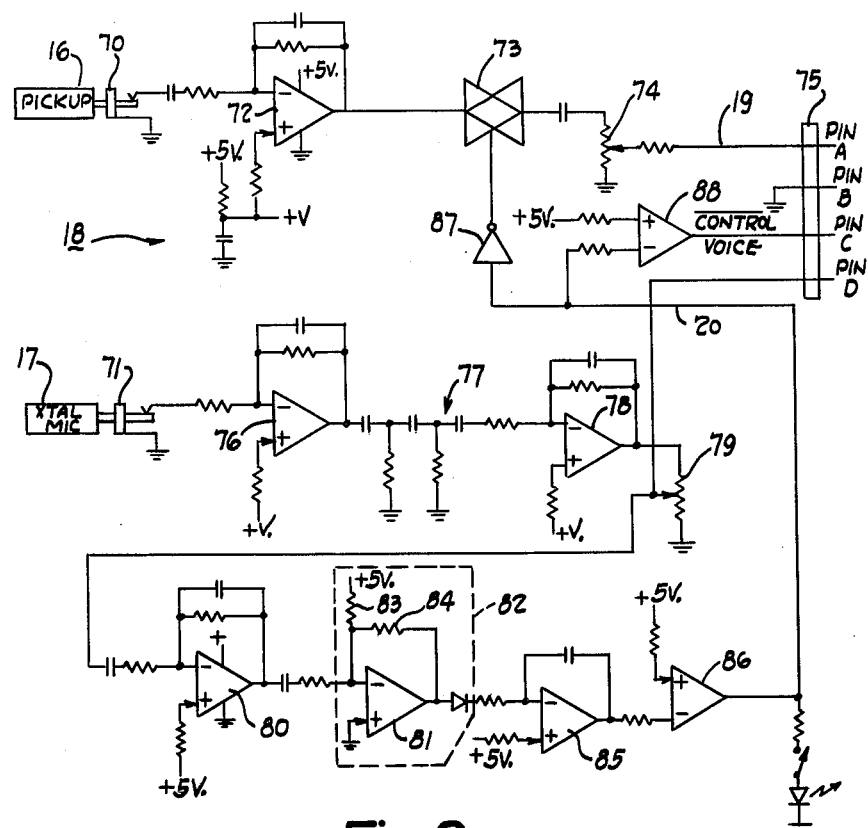
FIG. 2 is a schematic diagram of the distant voice unit.

FIG. 2 is a schematic diagram of the distant voice unit 18. This distant voice unit adapts the apparatus 15 to monitor the conversation on the other end of the line. The apparatus 15 therefore can be set up in one location and distant voices can be analyzed over the telephone.

If two persons are having a face-to-face dialogue, then a directional microphone for the subject would be in a jack 70, and a directional microphone for the interviewer would be plugged into jack 71. If a two channel recording of a previous dialogue has been made, then, similarly, the subject's voice signal is fed to jack 70 and the interviewer's voice signal is fed to jack 71.

In FIG. 2 the distant voice is picked up on pick-up 16, supplied through jack 70 and amplifier 72 and through an analog switch 73 and a volume adjusting potentiometer 74 to an output pin A of an output connector plug 75. The local voice on the microphone 17 causes the analog switch 73 to open, thus blocking both voices from going through the output connector plug 75.

The local voice on microphone 17 is thus a controlling signal to control whether the distant voice is passed through to the remainder of the apparatus. This local voice on microphone 17 passes through jack 71, a buffer amplifier 76, a high pass filter 77 and another amplifier 78 to a potentiometer 79 which adjusts the level of the local voice. The high pass filter 77 removes any 60 to 120 hertz noise present because of the power supply. The signal passes through another amplifier 80 and then to an amplifier 81 which is a part of a rectifier circuit 82 which amplifies that part of the signal which exceeds a threshold established by the operating voltage, e.g. +5V, and threshold resistor 83 and feedback resistor 84. An amplifier 85 connected as an integrator circuit receives the positive half cycles from the rectifier and passes them to a comparator 86. When a local voice is present, the integrator 85 receives positive half cycles from the rectifier 82 causing the integrator 85 to go low and the comparator 86 to switch high. When the comparator is high, the signal is applied through an inverter 87 to be a low and this is the control voltage applied to the analog switch 73 thus preventing the pick-up 16 signal from going to the output connector plug 75. When the output of inverter 87 is high; namely, no local voice, then the distant voice from pick-up 16 can be passed through to plug 75. Ground is provided on pin B of plug 75 which is a ground only by connection to the rest of the apparatus 15 and this prevents noise generated by the tape recorder power supply from being fed through a ground loop. An inverter 88 is also connected on the output of the comparator 86 and supplies a $\overline{\text{CONTROL VOICE}}$ signal on pin C of plug 75. A LOCAL VOICE signal is supplied on pin D of plug 75 from the potentiometer 79. Line 19 on FIG. 1 is pin A of plug 75 of FIG. 2. Line 20 on FIG. 1 is the inverse of the $\overline{\text{CONTROL VOICE}}$ signal on pin C of plug 75. Line 20 is the output of the comparator 86 before it is inverted by inverter 88.

Figure 3:
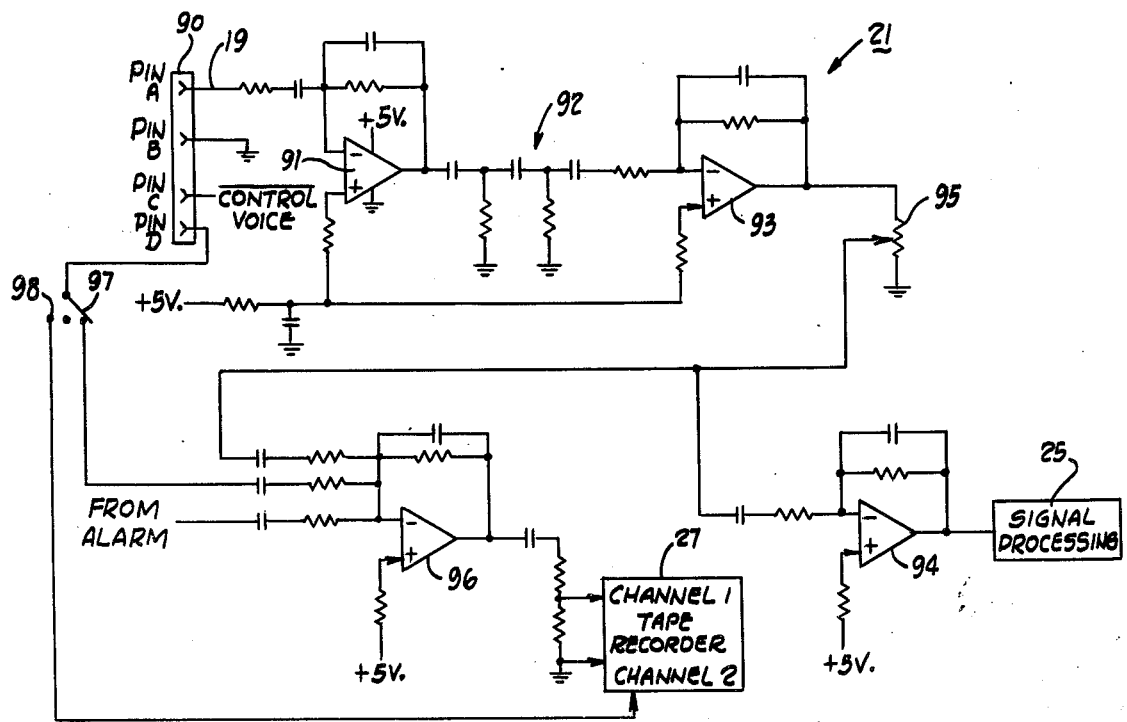
FIG. 3 is a schematic diagram of the amplifier section.

FIG. 3 illustrates the amplifier section 21 and it has a jack connector 90 to receive the plug connector 75 from the distant voice unit 18. Pins A, B, C and D are provided in this jack connector to receive the signals from the like designated pins in the plug 75. The distant voice signal on line 19 or pin A, is amplified by an amplifier 91 and passed through a high pass filter 92 which eliminates 60 and 120 hertz noise. This signal, which is still an analog signal, is passed through amplifiers 93 and 94 to the signal processing section 25. After amplifier 93 a potentiometer 95 is provided which is used to adjust the volume of the distant voice signal. From this potentiometer 95 the signal is also fed to another amplifier 96 and through it to the optional tape recorder 27. The alarm 49, when it sounds, is fed to the tape recorder 27 through this same amplifier 96. If it is desired to record both sides of the conversation, not merely the distant voice, then a switch 97 may be moved to the position shown to supply the local voice on pin D through the amplifier 96 to the tape recorder 27. If the tape recorder is a two-channel type, as shown, then switch 97 may be moved to a position 98 to record the local voice on the second channel.

Figure 4:
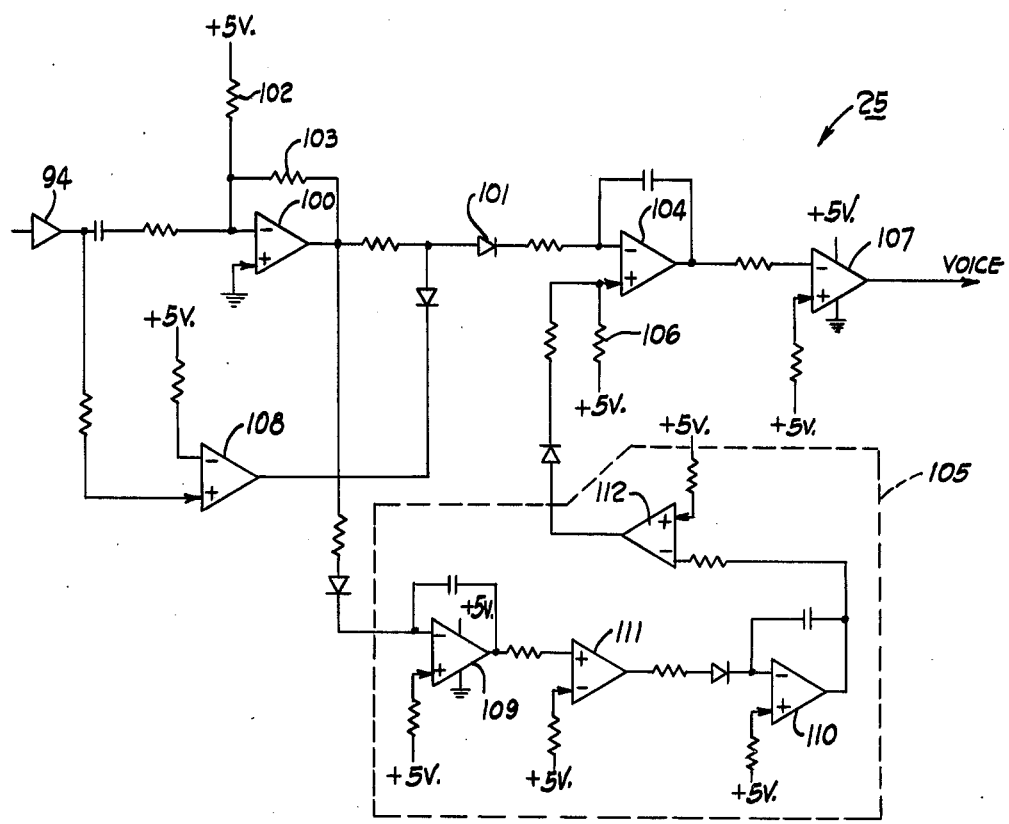
FIG. 4 is a schematic diagram of the signal processing section.

FIG. 4 shows the signal processing section 25, and the signal is received from the amplifier 94 of FIG. 3. The analog signal is supplied to an amplifier stage 100 and then through a diode 101 to an integrator 104. Resistors 102 and 103 again set a threshold and if the incoming signal's negative amplitude exceeds this threshold, the difference is multiplied in the amplifier 100 and inverted. This amplified signal is passed to the integrator 104 which is normally disabled by a disabling circuit 105. This disabling circuit determines the length of time of the signal, and if it is present for a continuous period, for example, 60 milliseconds, it is recognized as being VOICE, and the integrator 104 is enabled. When the integrator becomes enabled, the output voltage thereof falls with each incoming peak, but due to the resistor 106 on the non-inverting input, the output voltage rises slowly in the absence of signal. If the signal is strong enough, its value exceeds the threshold of a comparator 107 and VOICE goes high.

A comparator 108 is connected essentially in parallel with the amplifier 100 and this comparator 108 detects whether the amplifier 94 has saturated to ground. If it has, the output of amplifier 108 pulls the rectified signal output through diode 101 toward ground thus preventing loud noises from passing to the integrator 104.

The disabling circuit 105 consists of two integrators 109 and 110 and two comparators 111 and 112. When signal peaks appear from the amplifier 100, the integrator 109 goes low rapidly. It rises slowly when the signal disappears. If the incoming peaks are close together the output remains low and the first comparator 111 presents a constant ground to the next integrator 110 so long as signal is present. The second integrator 112 has a signal which rises slowly due to the large value resistor on the non-inverting input thereof. If the signal continues for a certain period of time, for example, 60 milliseconds, it reaches the threshold of the second comparator 112 and the main integrator 104 is enabled. If a few incoming peaks are missing, then the first integrator 109 charges high, causing the comparator 111 to go high and forcing the second integrator 110 to rapidly go low, thus reinitializing the disabling circuit 105. The VOICE signal is a digital signal which is high when the subject is speaking and low when there is silence.

Figure 5:
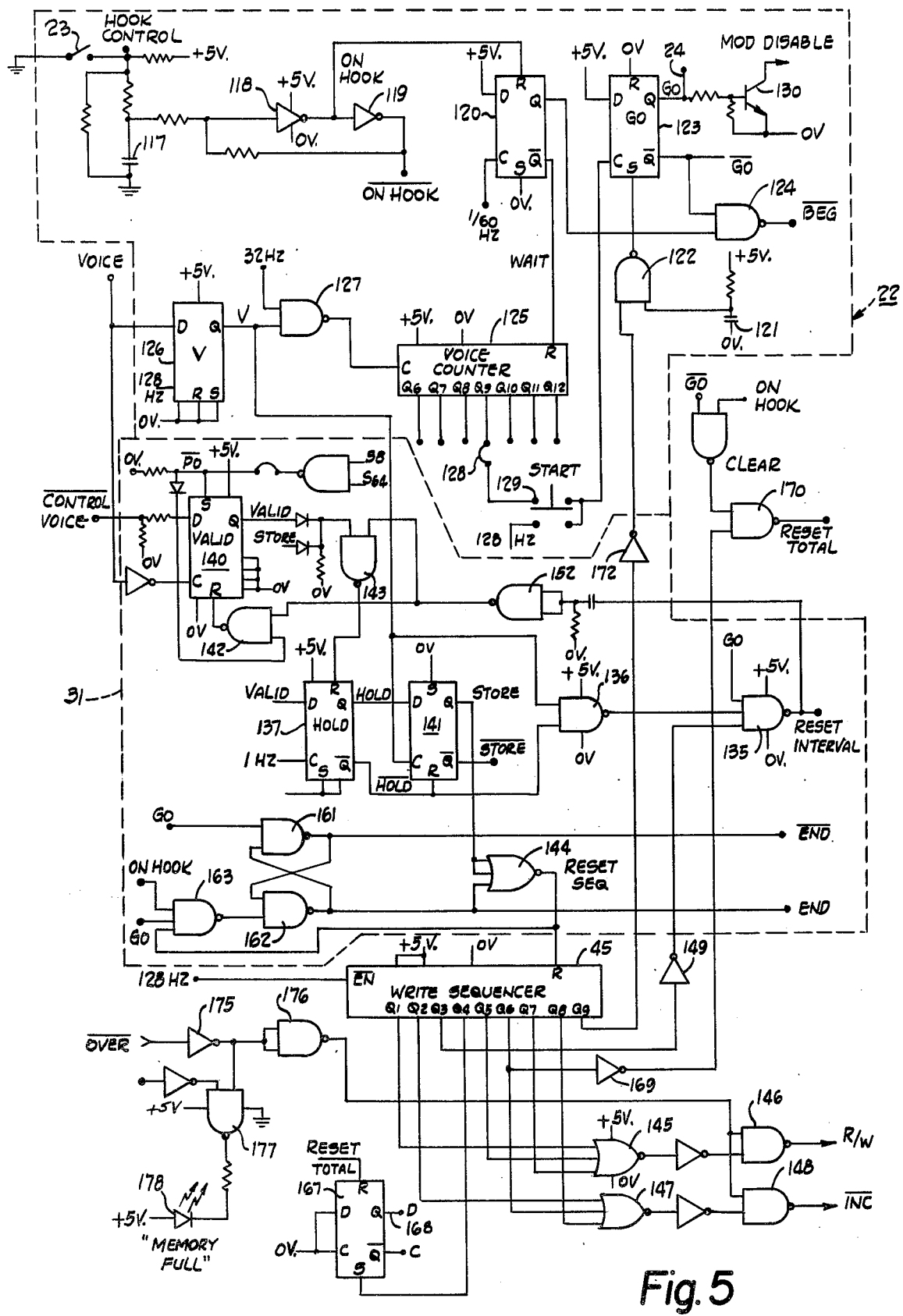
FIG. 5 is a schematic diagram of the start up, voice timing control and interval write sequencer portions of the circuit.

FIG. 5 shows mostly the control logic associated with the voice fluency apparatus 15 and includes generally the start-up control 22 at the upper part of FIG. 5, the voice timing control 31 in the center and the write sequencer 45 at the lower portion of FIG. 5. When the telephone receiver is picked up, the ON HOOK switch 23 opens and the delay of a given period, for example, 30 seconds, is initiated. At the end of this period another delay, for example, 8 seconds of talking on the telephone is required before the apparatus 15 becomes active. After these two delay periods the data can be stored in the memory module 32, the stop light unit 37 becomes active, the feedback to the individual becomes active and the tape recorder, if used, is turned on. The 30 second and voice dependent delays prevent the unit from becoming prematurely active when initiating a phone call. This delay allows time for dialing as well as delays that may occur when going through a switchboard or receptionist, thus insuring a conversation is well underway before the apparatus is activated.

FIG. 5 illustrates the start-up control circuit 22 which provides a start-up sequence. When the telephone receiver is picked up, the ON HOOK switch 23 opens causing HOOK CONTROL to go high. This switches on power to the memory module 32 through line 62, FIG. 1. Power is also supplied to the telephone unit which is the apparatus of FIGS. 2–10. Inverter 118 establishes an ON HOOK signal temporarily high, because a capacitor 117 has not yet charged, and an inverter 119 establishes a $\overline{\text{ON HOOK}}$ to be temporarily low. The ON HOOK temporarily high signal causes a WAIT flip-flop 120 to be reset therefore the WAIT line is high. An initially discharged capacitor 121 acts through a NAND gate 122 to reset a GO flip-flop 124 causing the GO line 24 to go low which in turn resets the total counter 34 and interval counter 30, FIG. 1, and makes END go low. As noted below this selects the interval count to the memory module 32.

Figure 6:
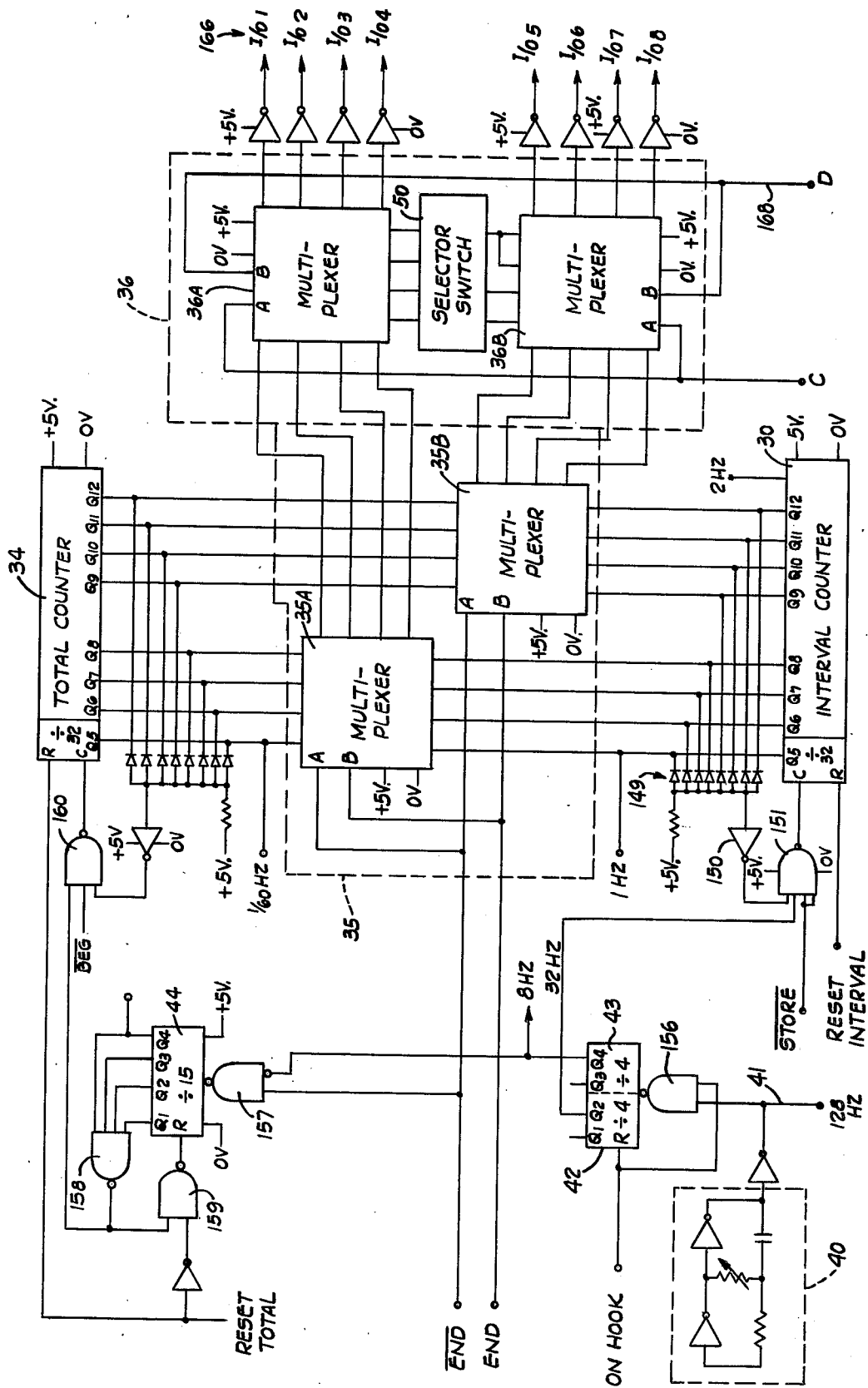
FIG. 6 is a schematic diagram of the counter and multiplexer portions of the circuit.

When the total counter 34, FIGS. 1 and 6, reaches a preset period for example, 30 seconds, it causes the WAIT flip-flop 120 to be clocked causing WAIT to go low. This disables the total counter 34 via a NAND gate 124 which has an output $\overline{\text{BEG}}$ which is connected to control this total counter 34. The clocking of flip-flop 120 also enables a voice counter or initial start-up sequencer 125.

When there is talking by the subject, VOICE is high and this supplies the D input to a data type flip-flop 126 making the Q output thereof high to supply a V signal as also being high. This high signal is fed through a NAND gate 127 to allow the voice counter 125 to count. The first five outputs of the voice counter 125 are not shown but the last seven outputs Q6–Q12 are shown giving selective outputs of one second up through 64 seconds. A jumper 128 may be connected to any one of these outputs and the eight second output is selected for an eight second delay. This is connected through a manual start switch 129 to the clock input of the GO flip-flop 123. When the count on the jumper selected output, e.g., eight seconds, goes high, it causes the GO flip-flop 123 to be clocked and the GO line 24 goes high. This causes a transistor 130 to conduct and MOD DISABLE is grounded which allows the memory module 32 to respond to the R/W and $\overline{INC}$ outputs. The total counter 34 is enabled via $\overline{BEG}$, the interval counter 30 is now under control by VOICE, and the tape recorder 27 is powered.

An interval write sequence is established by the control logic of FIG. 5. When VOICE and V are high, the interval counter 30 remains reset. This is described below in connection with the description of FIG. 6 and is established by a NAND gate 135 having the output labeled RESET INTERVAL. The V signal is supplied to NAND gate 135 through a NAND gate 136. When V goes low, the interval counter 30 starts counting and when it reaches a given delay period, it clocks a HOLD flip-flop 137. This given delay period is presettable and as described below has been set as one-half second. This one-half second is taken from the interval counter 30. The interval is the pause or hesitation pause in the speech of the subject. Over ten years experience with analyzing the speech of subjects has shown that half second pauses are significant and one second pauses are even more significant. As will be shown below, the memory module will record all those pauses which are longer than one-half second and the stop light unit 37 is responsive to those pauses which are one second or more in length.

As described below for FIG. 6, a tap is taken off the one hertz output of the interval counter 30 and this is applied to the clock input of the HOLD flip-flop 137. This is a total cycle time of one second and hence after a one-half second delay the signal goes high clocking in the logic level on the D or data terminal. This is VALID obtained from a VALID flip-flop 140. The $\overline{CONTROL}$ is connected to the data input of flip-flop 140 and this $\overline{CONTROL}$ must be high, which means that the doctor or interviewer of the subject must be silent, when VOICE goes low. This causes flip-flop 140 to be clocked high and VALID goes high. After a one-half second delay HOLD goes high as flip-flop 137 is clocked. When VOICE goes high again, V goes high and clocks a STORE flip-flop 141 so that STORE goes high, resulting in data being taken. While the doctor and patient are both silent, that is, when VOICE is low, $\overline{CONTROL}$ voice is high and VALID is high, if the doctor's voice comes on, $\overline{CONTROL}$ voice goes low. The flip-flops 140 and 137 are reset so that VALID and HOLD go low and nothing will happen when VOICE goes high again.

In greater detail, when the doctor and patient have both been silent, i.e., when VOICE is low, $\overline{CONTROL}$ voice is high and VALID is high, if the doctor's voice comes on, $\overline{CONTROL}$ voice goes low. This acts through NAND gate 142 to reset the VALID flip-flop 140 causing VALID to go low and this acts through NAND gate 143 to reset the HOLD flip-flop 137. The resetting of these flip-flops means that nothing will happen when VOICE goes high again. This control circuit assures that the doctor is the one who must go quiet first to determine a true hesitation pause, which is defined as a joint silence of both parties bounded by speech of the subject.

When V goes low this means the output of gate 136 goes high and the output of gate 135 goes low so RESET INTERVAL is low and this means that the reset on the interval counter is discontinued permitting the interval counter 30 to start counting. As stated above, when it reaches one-half second it clocks the HOLD flip-flop 137 to make HOLD go high. When V goes high and HOLD is not high, this means that the pause interval is less than one-half second, then the interval counter 30 is reset because a $\overline{HOLD}$ is high, which is passed through gates 136 and 135 so that RESET INTERVAL is high. However, if HOLD is high, the flip-flop 141 is clocked high and STORE goes high. STORE causes the interval counter to be disabled, as shown below in connection with FIG. 6. Also, the high on STORE is passed through a NOR gate 144 so that RESET SEQ. goes low thus initiating the interval write sequence by removing the reset from the write sequencer 45. As this sequencer 45 counts, a high output appears on only one output and moves from Q1 to Q9 on the output thereof. Q1 generates a write command and Q2 generates an increment command. If $\overline{OVER}$ is high, indicating the memory module 32 is not full, the output from Q1 passes through a NOR gate 145 and a NAND gate 146 to the R/W output which is a read/write command. When this R/W line is low it writes this pause interval time into the memory module 32. The increment command from Q2 of sequencer 45 passes through a NOR gate 147 and a NAND gate 148 to the $\overline{INC}$. output, which causes the memory to be incremented to a new address which occurs after each write command. Because the interval is always selected to the memory module 32 except during the end of call sequence, its contents are written in the memory. Output Q3 of sequencer 45 is connected through an inverter 149 to the gate 135 and causes RESET INTERVAL to go high which acts via gates 152 and 143 to reset HOLD, which resets STORE, and RESET SEQ. goes high again.

Both the interval and total counters 30 and 34 have circuitry to stop the count at all ones on the outputs. The diodes 149 and inverter 150, FIG. 6, act as a NAND gate, and act through another NAND gate 151 to stop the clock input to the interval counter 30.

The V flip-flop 126 is used to prevent race conditions from occurring which could result in all zeros being written into the memory module 32. This could happen if the VOICE caused RESET INTERVAL to go high at the time HOLD is clocked high, followed by VOICE going low and high within one-half second. Because V can change only at a known time, this cannot occur.

FIG. 6 illustrates the main oscillator 40 having an output at the clock frequency line 41 which supplies 128 hertz, for example, to several places so labeled on the circuit diagram. This clock frequency is supplied through a NAND gate 156 when the telephone receiver is not on the hook to a counter or divider 42, 43. Divider 42 divides by four to provide a 32 hertz signal to the NAND gate 151. Divider 43 divides again by four to supply an 8 hertz signal through a NAND gate 157 to the divide by 15 divider 44. This divide by 15 is accomplished by resetting the divider 44 through NAND gates 158 and 159 when the Q1–Q4 outputs of divider 44 are all high, thus skipping one logic state. The total counter 34 has an input to the clock input thereof at 8/15 hertz through a NAND gate 160 and the front end of the total counter 34 divides by 32 so that 1/60 hertz appears on the Q5 output of counter 34. This 1/60 hertz output was supplied to the WAIT flip-flop 120 in FIG. 5. In a similar manner the 32 hertz frequency is supplied to the clock input of the interval counter 30 and the Q5 output thereof is a divide by 32 divider to have one hertz on the output thereof. As stated above, this is supplied to the HOLD flip-flop 137 in FIG. 5.

The control logic shown in FIGS. 5 and 6 establishes an end of call sequence. This means the sequence of events which happens when the telephone receiver is placed back on the hook at the completion of the dialogue. With GO high, the apparatus 15 will remain powered up after the receiver goes on hook until it has gone through its end of call sequence. When the receiver goes on hook, ON HOOK switch 23 is closed, HOOK CONTROL goes low and ON HOOK goes high causing the frequency dividers 42–44 and therefore the total counter to be disabled.

Near the lower middle of FIG. 5 two output terminals are labeled END and $\overline{END}$. These are fed by NAND gates 161 and 162 with gate 162 fed from a NAND gate 163. Gate 163 has an input from the RESET SEQ. so if the write sequencer 45 is in the process of writing an interval, with its reset terminal low and RESET SEQ. low, this will disable gate 163 so that the write sequencer 45 is undisturbed. Once RESET SEQ. is high, END goes high through gates 163 and 162, causing RESET SEQ. to go low thus allowing the end of call sequence to start. END going high also selects the total count to the memory module 32. Prior to this time it will be realized that each time there was a pause interval of a half second or more, the write sequencer 45 initiated a read/write command and increment command so that these signals were passed to the stop light unit 37 and the memory module 32. Memory module 32 has internal circuitry to be incremented to a different address so that there is stored in each address of the memory a length of time of that particular hesitation pause. Now at this end of call, the memory is to be supplied with the total count; namely, the length of time of the entire telephone conversation. FIG. 6 shows that the counter multiplexer 35 are broken into two parts 35A and 35B, each of which has an input terminal B connected to the line END. When END goes high this signal on the B input terminals of the multiplexers causes the multiplexers to supply the total count from the outputs Q5–Q12 of the counter 34 to the second or output multiplexer 36. It passes through these multiplexers to the input/output terminals 1–8 with reference number 166. From here they pass to the stop light unit 37 and memory module 32. The memory module 32 receives a write command from Q1 of sequencer 45 and then receives an increment command from Q2 of sequencer 45. The Q4 of sequencer 45 then sets a flip-flop 167 which makes the Q output 168 thereof go high. FIG. 6 shows this line 168 as applied to the B terminals of the second multiplexer 36A and 36B which supplies the binary code of the setting of the selector switch 50 to the memory module 32. The sequencer 45 continues to sequence and from Q5 of 45 a write command is given and then from output Q6 an increment command is given. The write command from Q5 writes into the memory the selector switch code and the increment command from Q6 of 45 resets the total counter 34. This occurs because the Q6 output goes through an inverter 169 to a NAND gate 170 and the output goes high which is RESET TOTAL. FIG. 6 shows that this is connected to the reset terminal of the total counter 34. This is also connected to the reset terminal of the flip-flop 167 and the Q output 168 thereof reselects the total counter 34. This counter has previously been reset so that it now contains all zeros. Another write command is given from Q7 of sequencer 45 and this causes all zeros to be written into the memory from the total counter and next another increment command is given from Q8 of 45. The last step of the sequencer 45 from output Q9 resets GO. This output from Q9 goes through an inverter 172 to the NAND gate 122 to reset the GO flip-flop 123. GO is now low and this causes MOD DISABLE to go high as well as the system power to be shut down, except for battery charging, not shown.

FIG. 5 also shows at the lower left a circuit which determines when the memory module 32 is full. As long as the memory is not full then $\overline{OVER}$ is high. This passes through two inverters 175 and 176 to be a high on the NAND gate 146 and enable that gate. However once the memory is full, then $\overline{OVER}$ is low passing through the two inverters 175 and 176 to disable NAND gates 146 and 148 and thus prevent any more read/write commands from passing to the memory. Also this low on $\overline{OVER}$ passes through inverter 175 and a NAND gate 177 to be a low on the output thereof and hence illuminate the light emitting diode 178 indicating that the memory is full.

Figure 7:
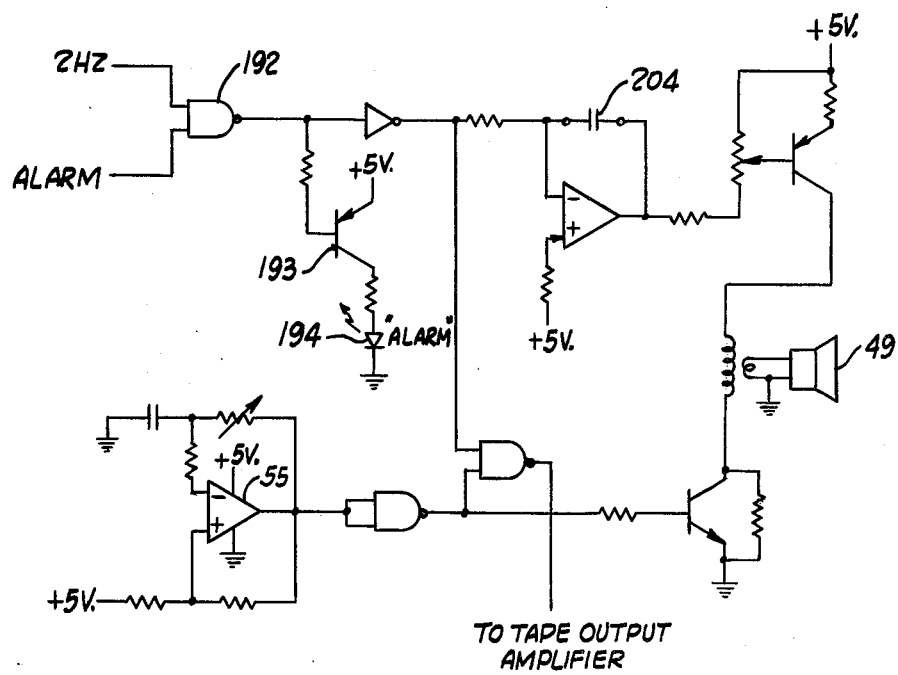
FIG. 7 is a schematic diagram of the alarm output section.
Figure 8:
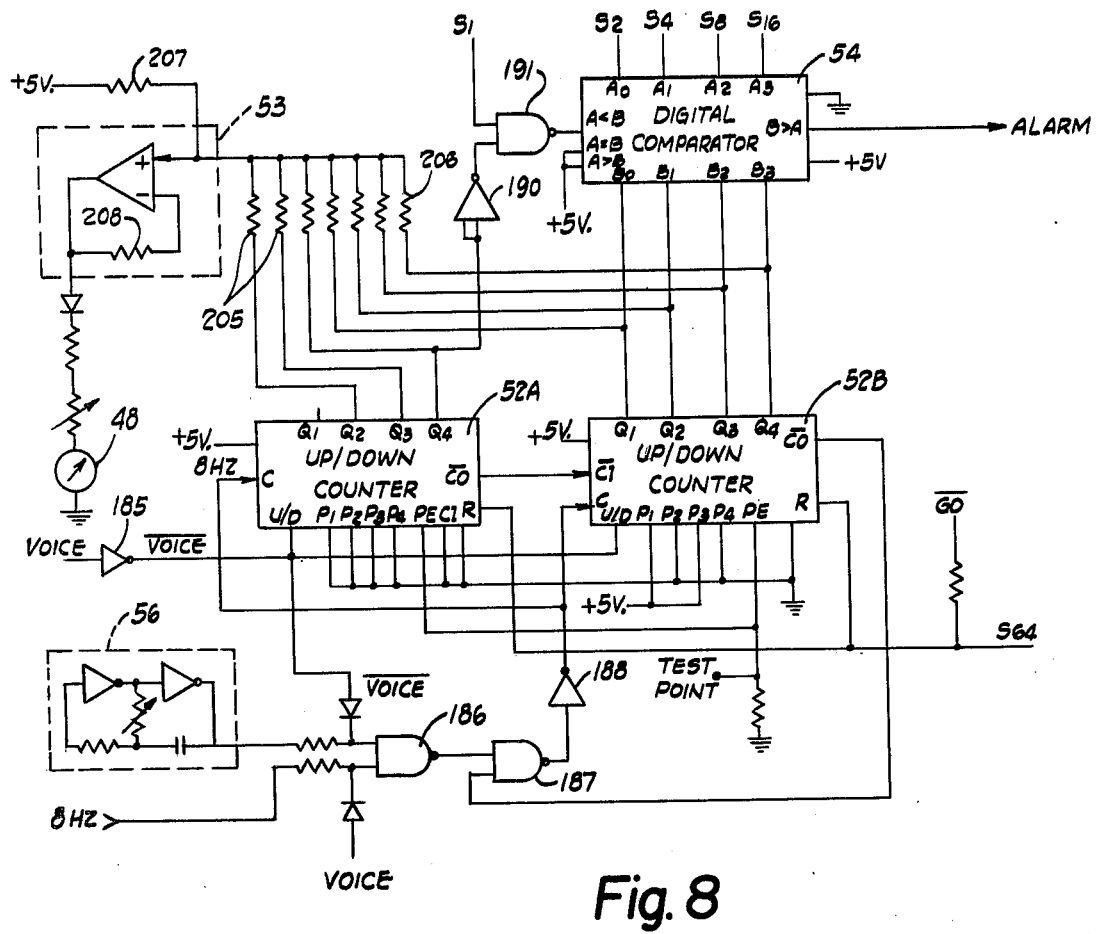
FIG. 8 is a schematic diagram of the meter control section.

FIGS. 7 and 8 illustrate the meter and alarm logic. This portion of the circuit centers around the up/down counters 52A and 52B. VOICE is supplied through an inverter 185 to the up/down terminal U/D of these up/down counters. VOICE not only determines whether the count is up or down, but also the clock frequency used. The voice oscillator 56 is shown in FIG. 8 and is supplied to one input of a NAND gate 186 and through it to another NAND gate 187 and an inverter 188 to the clock inputs of the up/down counters 52A and 52B. When VOICE is low, the count is up and the voice oscillator input is disabled by $\overline{VOICE}$ being high, so the 8 hertz input is used. When VOICE is high this disables the 8 hertz input to gate 186 and the voice oscillator 56 is used for counting down, at a different rate, which may be a faster rate.

The digital comparator 54 has inputs from the selector switch 50 and provides an ALARM output which is high when the code S1–S16 from selector switch 50 is less than the count of the up/down counter 52. The Q4 output of counter 52A is connected through inverter 190 and NAND gate 191 to the A<B input terminal of the comparator 54, which is used to carry in the lower order comparison of S1 from the Q4 output of counter 52A. The Q1–Q4 outputs of counter 52B are connected to the B0–B3 inputs of the comparator 54.

FIG. 7 shows that ALARM is connected through a NAND gate 192 and 2 hertz is also connected through this same NAND gate and through a transistor 193 to cause an LED lamp 194 to flash at a 2 hertz rate as an alarm indication. The output of the NAND gate 192 also enables the alarm oscillator 55 to energize the audible alarm 49.

Figure 9:
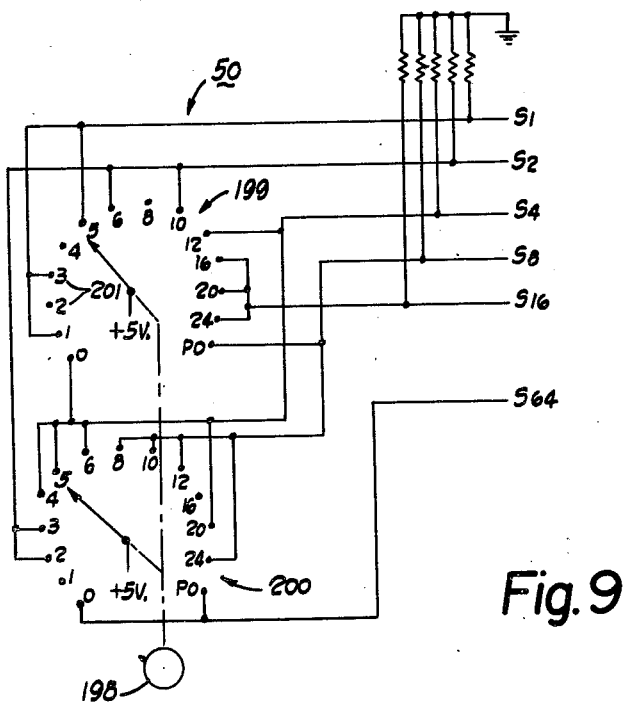
FIG. 9 is a schematic diagram of the delay selector switch.

FIG. 9 illustrates the delay selector switch 50. A knob 198 turns two gangs 199 and 200 of a rotary selector switch. Indicia 201 indicates the number of seconds of delay desired before the alarm will be initiated after the subject becomes silent. A high level logic condition, e.g., +5 volts is supplied to the movable switch blades and the various contacts are connected to S1, S2, S4, S8, S16 and S64 switch outputs. The delay switch is shown in a five second delay position, as an example, and in such case switch lines S1 and S4 are high. Thus the selector switch 50 is in essence a decade to binary code converter. This binary code is that which is selected when the B terminal of the output multiplexer 36 goes high to supply this selector code to the input/output terminals 166 and through them to the memory module 32 and stop light unit 37.

In a practical circuit constructed in accordance with the present invention all of the operational amplifiers were Norton amplifiers using the LM 3900. The outputs of these amplifiers go high when the current flowing into the non-inverting input, which looks like a diode, is greater than the current flowing into the inverting input. The current in the alarm oscillator 55 non-inverting input was about 0.45 microamperes when the output was low and about 0.9 microamperes when it was high. The capacitor 204 of the alarm oscillator 55 charged up until the current in the inverting input was 0.9 microamperes and charged down until it was about 0.45 microamperes.

In FIG. 8 digital to analog converter 53 consists of another Norton amplifier and weighted resistors, such as resistors 205 and 206. A resistor 207 is used for biasing so that when the weighted resistors are at ground potential the voltage at the non-inverted input of converter 53 is equal to one diode drop above ground. Without this resistor 207 the output would not respond to the first few counts. The feedback resistor 208 for example 47 K ohms, converts the equivalent negative input current to a voltage.

Figure 10:
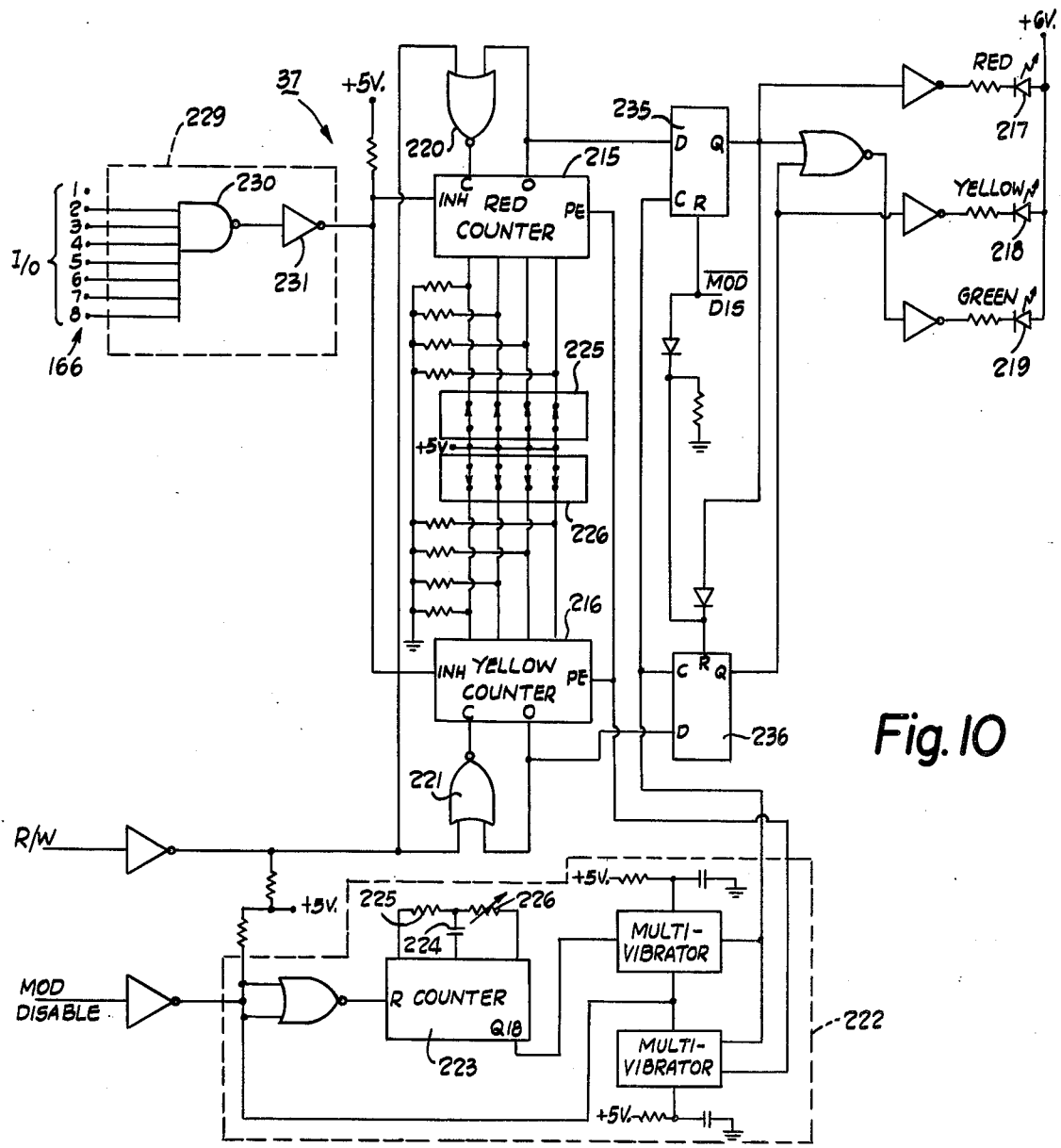
FIG. 10 is a schematic diagram of the stop light unit.

FIG. 10 illustrates the stop light unit 37 and indicates whether the patient or subject is pausing too much. A red light indicates he is pausing too much, a green light indicates he is not, and a yellow light indicates a borderline condition. The thresholds for the lights can be programmed by a switch bank inside the unit.

FIG. 10 shows that the input/output terminals 166 supply inputs to this stop light unit 37. A red counter 215 and a yellow counter 216 count the number of pauses required for the red light 217 to be illuminated and for the yellow light 218 to be illuminated, respectively. A green light 219 is illuminated if neither of lights 217 or 218 are illuminated. The counters 215 and 216 have clock inputs from NOR gates 220 and 221, respectively, with each of these having an input from the R/W input. A timer 222 is used to select a timed period, e.g., two minutes, during which the number of pauses in that timed period will be counted. The timer 222 includes a divider 223 which has a feedback capacitor 224 and feedback resistor 225 plus a potentiometer 226 to cause it to oscillate as an astable multivibrator at some given frequency, for example 2.18 kilohertz. The counter 223 counts down by some factor, for example, $2^{18}$ to give the desired square wave time period, for example, two minutes. This timed period is supplied to the preset enable terminal PE of the red and yellow counters 215 and 216.

A switch bank 225 is connected to the input of the red counter 215 and a switch bank 226 is connected to the input of the yellow counter 216. Each of these switch banks includes four single throw switches which may be manually preset. To program the number of pauses for the red light, these variables are programmed in binary code by manually actuating these switch banks. A switch closed condition is a high and a switch opened condition is a low. Any number of pauses between 1 and 15 may be set for either the yellow or red. If the value for the red light is not greater than the value for the yellow light, the yellow light will never come on.

The pause length input from the interval counter 30 goes through the input/output terminals 166 to a comparator circuit 229 made up of a NAND gate 230 and an inverter 231. It will be recalled that the incoming signals on the input/output terminals 166 are in half-second increments, that is on I/O 1 there is a half-second signal, on I/O 2 there is a one-second signal, on I/O 3 there is a two-second signal, and so on according to binary code progression. The signals on the I/O terminals 166 are low true binary signals, meaning that a zero second input is 11111111, a one-half second input is 11111110, a one second input is 11111101, and so on. The comparator circuit 229 produces a low output on the output of the inverter 231 if the hesitation pause length is one second in length or greater. If the incoming pause is less than one second in length, the red and yellow counters 215 and 216 are inhibited by a high on the output of NAND gate 231 being applied to the inhibit terminals of these counters.

After a pause in speech, the R/W input goes high, clocking the red and yellow counters 215 and 216. Also if the length of the pause is more than one second in length, the counters 215 and 216 are not inhibited and the count will decrement. These are down counters and when the number of pauses equals the number programmed on the switch banks 225 and 226, respectively, the count will go to zero and the zero output of the respective counter will go high. When the count is zero, further counting is inhibited through the gates 220 or 221 for the duration of the two minute interval.

When the square wave two minute timed period from counter 223 goes low, D flip-flops 235 and 236 are clocked storing the state of lamps 217–219 for the next two minutes. Then the counters 215 and 216 are preset to the numbers on the switch banks 225 and 226, repeating the entire process for the next two minutes.

In one practical electronic circuit embodying the invention, the component types were as follows:
Op amps — Norton LM 3900
Counter 30, 34 — Type 4040
Multiplexer 35, 36 — Type 4519
Counter 52 — Type 4516
Comparator 54 — Type 4585
Sequencer 45 — Type 4017
Counters 215, 216 — Type 4526
Counter 223 — Type 4521

The above description of the operation of the voice fluency apparatus 15 shows that it will determine the fluency of uttered speech of a human subject. Microphones or pickups 16 and 17 may be used as transducers and responsive to the voice of a subject and of an interviewer who may be a doctor, for example. The voice timing control 31 may be considered to be pause means to determine hesitation pauses of absence of vocal sounds which pauses are in excess of a time interval in the order of one second of time. This period of time might be from one third of a second up to three seconds and still be in the order of one second of time. If one desires only one and one-half second and longer hesitation pause intervals, then the I/O 2 terminal would be disconnected from the input of the NAND gate 230. Conversely, if half second and longer hesitation pause intervals are desired to be counted, then the I/O 1 terminal should be connected to the input of the NAND gate 230.

The red and yellow counters 215 and 216 of the stop light unit 37 may be considered the counter for determining the number of such hesitation pauses. The two-minute timer 222 determines a period of time during which the hesitation pauses are counted. For example, if the switch bank 225 is set at the number 4, then the red counter 215 will count down from 4 to 0. If it reaches this count within the two-minute period, this determines the rate of hesitation pauses, and the red light 217 will be illuminated to show the rate of hesitation pauses to be two pauses or more per minute; namely four pauses in the two-minute time period.

That part of the voice timing control circuit 31 which includes the VALID flip-flop 140 is that which insures that the doctor or interviewer must be quiet first before the hesitation pause is a valid hesitation pause. This means that the apparatus will ignore those pauses which are between the control voice and the subject's voice or between the subject's voice and the control voice and will also ignore those pauses which are entirely within the control voice speech of the doctor or interviewer. Thus this circuit obtains true hesitation pauses of the subject.

The background investigations for the development of the identification of true hesitation pauses was stimulated by the work of R. Rosenman and M. Friedman who called attention to the importance of psychological factors in the development of clinical coronary atherosclerosis. They described Type A personality as exhibiting (1) an intense, sustained drive to achieve self-selected but usually poorly defined goals, (2) profound inclination and eagerness to compete, (3) persistent desire for recognition and advancement, (4) continuous involvement in multiple and diverse functions constantly subject to time restrictions (deadlines), (5) habitual propensity to accelerate the rate of execution of many physical and mental functions and (6) extraordinary mental and physical alertness. Subjects exhibiting an inverse pattern were classified as Type B. R. Rosenman and M. Friedman's global ratings were based on a combination of content and style. Type A style verbal responses were characterized as abrupt, emphatic, hurried and staccato. Hesitation pauses were not mentioned as stylistics in R. Rosenman-M. Friedman's original description of Type A.

To refine the R. Rosenman-M. Friedman technique, Dr. Herman K. Hellerstein and Dr. Ernest H. Friedman developed a new method of separate ratings of Type A content and style. It was found in the businessmen sample, that the top income group was significantly different from the middle income group but not significantly different from the bottom income group in terms of exhibiting more Type A style but not Type A content. These data suggesting Type A style correlates to lower coronary risk are discrepant with the R. Rosenman-M. Friedman hypothesis relating Type A (combined content and style) to higher coronary risk.

While 4½ and 8½ year followups of their prospective study demonstrate a higher coronary risk in the moderately hard-driving A's (A2), the extreme A's (A1) exhibited no higher risk than the B's (B3, B4). However, A's (A1 and A2) were at twice the risk of B's (B3 and B4). Thus, their findings implicate psychological stress acting independently of the standard coronary risk factors but do not yield practical guidelines for either the layman or his physician.

Since the methodology of rating interviews by auditioning content and style, separately or together, is highly subjective, a search was made for a more objective measure of Type A style. A common theme in the original Type A description was that of continuity of activity as reflected by the adjectives: "persistent, continuous, competitive, accelerated, and alert."

A review of psycholinguistics texts, suggested that the frequency of hesitation pauses is a valid measure of continuity of verbal activity. Factors influencing discontinuity include individual differences which are highly significant, the degree of prior learning, i.e., well-learned sequences have greater continuity and relating information of an intimate, embarrassing nature.

Verbal fluency is an aspect of speech style that an individual is not able to change easily. This observation is compatible with the impressions of E. H. Friedman from clinical psychiatry which indicate that an individual by way of either dissembling or acculturation is better able to mask or modify the content of his verbal responses than he can his style. Since the earlier investigations demonstrated less Type A style was correlated with higher coronary risk, the present invention supports the hypothesis that discontinuity, deceleration and decreased alertness measured as hesitation pauses provides an objective measure of Type A style indicative of maladaptive behavior and is correlated with higher coronary risk. Hesitation is considered to be particularly maladaptive since it represents immobility in the face of stress rather than the two preferable alternatives of fight or flight. Lack of hesitation reflects successful adaptation to stress expressed as continuity of verbal responses. Individuals with clearly defined goals who are bound for high attainment are less prone to hesitate while engaging in purposeful stress. This view is compatible at least in one respect with the original description of Type A as being oriented toward "poorly defined goals."

A hesitation pause was defined as joint silence of one second or more bounded by the speech of the subject. This was measured by auditioning with a stopwatch, the structured tape-recorded R. Rosenman-M. Friedman interviews of Cleveland businessmen and patent attorneys who were originally evaluated in 1965. The one-second time interval was the minimum time segment that could be measured with a stopwatch because of a limitation of the technician's reaction time in using the stopwatch; later studies of the same subjects utilizing electronic measurement of speech have shown less than one second intervals not to be of value in determining the degree of fluency.

Two population samples of middle-aged males were studied: 176 normal coronary prone, upper-middle class predominantly Jewish businessmen participating in the Case Western Reserve University-Jewish Community Center physical fitness evaluation program, and 106 predominantly non-Jewish patent attorneys representing over 90% of the total membership of the Cleveland Patent Law Association. The businessmen were classified by annual income and both samples were evaluated in terms of the standard coronary risk factors and by the R. Rosenman-M. Friedman Structured Tape-Recorded Interview designed to elicit Type A.

Taped interviews of the patent attorneys were analyzed using the R. Rosenman-M. Friedman global rating method based on a combination of content and style. Dr. Ray Rosenman, Dr. Herman K. Hellerstein and Dr. Ernest H. Friedman rated the patent attorneys' interviews simultaneously but independently in the same physical area on February 26 and 27, 1965. There was over 80% categorical agreement among the three doctors. A technician rated the interviews of the patent attorneys and the businessmen by separate ratings of content, style and the prevalence of hesitation pauses.

In 1975, subjects in both samples, their relatives, and their physicians were contacted by mail-out questionnaire and by phone to determine whether they were living or dead and their health status, with particular regard to coronary heart disease. The businessmen were invited to be restudied and 89 were reinterviewed as in 1965. Correlations between the prevalence of hesitation pauses in 1965 and 1975 demonstrated a high degree of reproducibility over time, $r=0.60$, $p<0.01$. This indicates that hesitation pauses have validity as a measure of behavior since validity is a function of reproducibility over time.

In the patent attorney sample, Rosenman rated 52 Type A and 54 Type B, based on his global rating according to the combination of content and style of responses to the 62 questions. Rosenman's ratings revealed a greater prevalence of a family history of coronary heart disease and fewer hesitation pauses in the Type A subsample. The latter finding confirms the hesitation pause as a valid measure of a facet of Type A behavior. Types A and B were identical in terms of the other standard coronary risk factors. This is consistent with an earlier report wherein it was demonstrated, using Rosenman's ratings, that serum cholesterol did not differ between Types A and B.

In both study populations, subjects with new coronary events during the previous ten years were compared with those who reported no such event or who died of other causes. Eight patent attorneys who reported new coronary events were compared with 81 non-coronary patent attorneys. Systolic and diastolic blood pressures were the most significant discriminators, $p<0.01$. The other standard risk factors were not able to identify future coronary cases. The hesitation pause was a significant predictor, $p<0.05$. Rosenman's global rating method selected only five of eight future coronaries which was not statistically significant whereas hesitation pauses selected seven of eight future coronaries, i.e., hesitation pauses are a significant predictor of coronary risk, since only one of the eight coronaries was a false negative.

In the businessmen, their 1965 hesitation pause ratings demonstrated that the top income group exhibited significantly fewer hesitation pauses than the middle group, but not significantly fewer hesitation pauses than the bottom income group, hence replicating the coronary risk pattern described earlier. In contrast with the patent attorneys, systolic and diastolic blood pressure among the businessmen exhibited only a trend towards statistical significance, $0.05<P<0.10$, in discriminating between 22 coronary and 148 non-coronary businessmen. As in the patent attorneys, the hesitation pause was statistically significant as a predictor, $p<0.05$, whereas separate ratings of Type A content and style and the standard coronary risk factors such as body weight, cigarette smoking, serum cholesterol and family history were not. Thus, blood pressure was a very significant predictor in the attorneys, $p<0.01$, but not in the businessmen, $0.05<P<0.10$.

Figure 11:
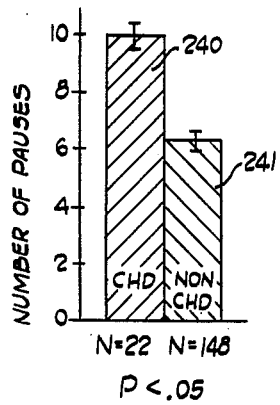
FIG. 11 is a graph of pauses of two groups of businessmen of higher and lower incidence of coronary heart disease.

Hesitation pauses were a significant predictor in both groups at the same level of significance, $p<0.05$. The hesitation pause is 75% accurate in these two study populations with 25% being false positives and false negatives. The average magnitude of risk in patent attorneys and businessmen comparing high hesitators versus low hesitators is three to one, whereas the R. Rosenman-M. Friedman global rating method is only two to one, Type A over Type B. FIG. 11 illustrates the number of hesitation pauses by the group of 176 businessmen. In the ten year period from 1965 to 1975, there were 22 new clinical coronary cases among these businessman. This is illustrated by the lefthand bar 240 on FIG. 11. The remaining group 241 of 148 businessmen did not have any clinical coronary atherosclerosis during that ten-year period. The left bar 240 indicates that among those 22 businessmen having coronary heart disease during that ten-year period, they had about ten hesitation pauses during the interview, whereas the non-coronary heart disease group of 148 businessmen had an average of only 6.3 pauses during their answers to this structured interview. This graphically illustrates that the number of hesitation pauses in the speech of a subject is a good indication of the proneness to clinical coronary atherosclerosis, because the probability of a person indicating by his speech that he is in one group yet he is actually in another group is only one in twenty; namely, the probability $p<0.05$.

Figure 12:
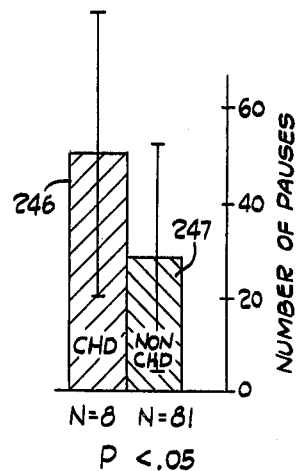
FIG. 12 is a graph of speech pauses in two groups of attorneys of higher and lower incidence of coronary heart disease.

FIG. 12 is a graph of the attorneys giving answers to the same structured interview series of questions. The bar 246 on the left is a graphical representation of the number of hesitation pauses within the speech of those eight attorneys who had coronary heart disease within the ten-year period from 1965 to 1975. They had about 51 hesitation pauses in the entire interview which lasted about 18 minutes, or about 2.69 pauses per minute. The bar 247 on the right side of FIG. 12 graphically represents the number of hesitation pauses within the speech of those attorneys who had no new coronary heart disease within the ten-year period from 1965 to 1975. The number of hesitation pauses was about 31 pauses in the 18 minute interview; namely, about 1.65 pauses per minute.

The ratio between the coronary heart disease and the non-coronary heart disease subjects is approximately the same for each of FIGS. 11 and 12, and again in FIG. 12 the probability of a person testing to be in one group yet actually being in the other group is only about 1 and 20; namely, the probability is less than 0.05.

The meter 48 gives an indication to the subject, if he is located at the telephone whereat the apparatus 15 is located, of the rate of hesitation pauses in his speech. The interval counter 30 counts the number of these pauses and the total counter 34 counts the total length of time of his entire speech. The needle of the meter 48 rises as the subject has a hesitation pause interval and falls as the subject speaks, thus this gives a continuous indication to the subject of the fluency of his voice pattern.

The alarm 49 further gives an indication to the subject of the fluency of his voice because if he has too many hesitation pauses in his speech, then the alarm 49 will sound.

The output of the output multiplexer 36 also contains data which indicates the rate of hesitation pauses in the speech of the subject, whether he is located at the apparatus 15 or located at some remote telephone. The input/output terminals 166 supply this data to the stop light unit 37 and to the memory module 32. The memory module may be used in conjunction with any kind of a recording apparatus such as a paper tape printer which prints a record of the data in the memory module 32. In one apparatus constructed in accordance with the invention this paper tape record included first, a consecutive listing of the time duration of each hesitation pause of the subject which pause was one-half second or longer in duration, second, the total length of time of the conversation, obtained from the total counter 34, third, the setting of the selector switch 50, and fourth, a series of all zeros, obtained from the output of the total counter 34, now reset, and this series of all zeros shows a separation of one conversation from the next conversation with a different subject. From the information in this memory module or from the paper tape print-out of the printer, one may readily obtain the number of pauses which are more than about one second in duration and obtain the total length of time of the conversation so that the rate of hesitation pauses per minute may readily be determined.

From the above it will be seen that the apparatus 15 is quite versatile both in use and application, being capable of use in a variety of ways in a medical setting and in other fields where speech fluency is desired.

CONCLUSIONS

Hesitation pauses have greater predictive value than does the R. Rosenman-M. Friedman global rating method of Types A and B, and is a valuable adjunct to the coronary risk profile. Hesitation pauses in both businessmen and patent attorneys occured at a rate greater than two times per minute among high hesitators, and less than once per minute among the most fluent subjects.

The purpose of the voice fluency monitor is to provide the primary care physician and cardiologist with an immediate assessment by telephone of the degree of hesitation in his patients while the patient is in his normal environment where distress may be more in evidence. Alerting the physician to hesitation in his patient can provide a more complete assessment of the individual's coronary risk and a greater awareness on the part of the treating physician of his patient's emotional state. This methodology has particular application for primary prevention in cardiology where early intervention is desirable. It also may have value for the evaluation of anxiety in psychiatric patients and for longitudinal follow of their response to psychotropic medication. This technique may also prove to have a place in the assessment of fluency in speech training courses.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of the circuit and the combination and arrangement of circuit elements may be resorted to without departing from the spirit and scope of the invention as hereinafter claimed.

What is claimed is:

1. The method of diagnosis of proneness to clinical coronary atherosclerosis in a human subject, comprising the steps of;
    having the subject utter oral speech,
    obtaining from said speech a determination of the hesitation pauses of absence of vocal sounds within the speech uttered by the subject which pauses are in excess of a given time interval in the order of one second of time,
    determining the number of such pauses in a period of time of speech of the subject,
    and indicating the subject's greater proneness to the development of clinical coronary atherosclerosis where the rate of such pauses is in excess of a value in the order of two pauses per minute.
2. The method as set forth in claim 1, including timing the hesitation pauses of the subject,
    discarding the pauses which are of shorter duration than said given time interval,
    and counting those pauses which are of longer duration than said given time interval.
3. The method as set forth in claim 1, including counting the number of hesitation pauses of the speech of the subject which are of longer duration than said given time interval which counting is for a given period of time to determine the rate of such pauses.
4. The method as set forth in claim 1, wherein said step of indicating includes a visible indicator.
5. The method as set forth in claim 1, wherein said step of indicating includes illuminating a red light upon the rate of such pauses exceeding a value of substantially two pauses per minute.
6. The method as set forth in claim 1, wherein the subject is uttering oral speech as part of a dialogue with another person.
7. The method as set forth in claim 6, wherein the hesitation pauses are pauses of joint silence of both parties and bounded by speech of the subject.
8. The method as set forth in claim 6, wherein the other person asks a series of questions,
    and the step of determining the number of hesitation pauses is determining the pauses of joint silence of both parties and bounded by the answers given by the subject to the questions propounded by the other person.

* * * * *

UNITED STATES PATENT AND TRADEMARK OFFICE
CERTIFICATE OF CORRECTION

PATENT NO. : 4,156,423
DATED : May 29, 1979
INVENTOR(S) : Ernest H. Friedman, et al.

It is certified that error appears in the above-identified patent and that said Letters Patent are hereby corrected as shown below:

Column 8, line 53, delete "124" and insert --123--.

Signed and Sealed this

Eleventh Day of September 1979

[SEAL]

Attest:

LUTRELLE F. PARKER
Attesting Officer    Acting Commissioner of Patents and Trademarks

UNITED STATES PATENT AND TRADEMARK OFFICE
CERTIFICATE OF CORRECTION

PATENT NO. : 4,156,423

DATED : May 29, 1979

INVENTOR(S) : Ernest H. Friedman, et al.

It is certified that error appears in the above–identified patent and that said Letters Patent are hereby corrected as shown below:

Under "References Cited" "PUBLICATIONS", Friedman, et al. the year "1960" should read --1968--.

Signed and Sealed this

Twenty-second Day of January 1980

[SEAL]

Attest:

Attesting Officer

SIDNEY A. DIAMOND

Commissioner of Patents and Trademarks